(12) United States Patent
Mashak

(10) Patent No.: US 8,573,248 B2
(45) Date of Patent: Nov. 5, 2013

(54) PNEUMATIC VIBRATION DAMPENING DEVICE

(75) Inventor: James N. Mashak, Madison, WI (US)

(73) Assignee: General Electric Company, Schenectady, NY (US)

( * ) Notice: Subject to any disclaimer, the term of this patent is extended or adjusted under 35 U.S.C. 154(b) by 427 days.

(21) Appl. No.: 12/963,099

(22) Filed: Dec. 8, 2010

(65) Prior Publication Data
US 2012/0145261 A1    Jun. 14, 2012

(51) Int. Cl.
*F16K 21/14*    (2006.01)
(52) U.S. Cl.
USPC .......................... 137/514.5; 137/534; 251/50
(58) Field of Classification Search
USPC ......... 137/514, 514.5, 514.7, 534; 251/48, 50
See application file for complete search history.

(56) References Cited

U.S. PATENT DOCUMENTS

| | | | | |
|---|---|---|---|---|
| 1,111,319 A | * | 9/1914 | Paulsmeier | 137/514.5 |
| 1,178,422 A | * | 4/1916 | Smolarek | 137/466 |
| 2,576,517 A | * | 11/1951 | Jurs | 137/469 |
| 3,034,731 A | * | 5/1962 | Chapin | 239/318 |
| 3,797,522 A | * | 3/1974 | Carleton | 137/528 |
| 4,257,452 A | | 3/1981 | Hill et al. | |
| 4,257,453 A | | 3/1981 | Kohnke | |
| 4,481,974 A | | 11/1984 | Schmitt et al. | |
| 4,537,216 A | * | 8/1985 | Schwartz et al. | 137/514 |
| 5,692,724 A | | 12/1997 | Champagne | |
| 6,443,180 B1 | | 9/2002 | Samuelson et al. | |

FOREIGN PATENT DOCUMENTS

| | | |
|---|---|---|
| GB | 563672 A | 8/1944 |
| GB | 1321499 A | 6/1973 |

OTHER PUBLICATIONS

Search Report and Written Opinion from corresponding EP Application No. 11191456.0 dated Apr. 12, 2012.

* cited by examiner

*Primary Examiner* — John Rivell
*Assistant Examiner* — Time Aigbe
(74) *Attorney, Agent, or Firm* — Andrus, Sceales, Starke & Sawall, LLP

(57) ABSTRACT

A gas flow valve having pneumatic vibration dampening device to reduce the vibrations created by the flow of gas through the gas valve. The gas valve includes a gas flow conduit that terminates at a discharge opening. A valve member is movably positioned relative to the discharge opening and allows gas flow in a flow condition and prevents the flow of gas in a seated position. The valve member includes a gas passage formed within the valve member. At least one flexible membrane is mounted to the valve member and surrounds an outlet opening of the gas passage. The flexible membrane is inflated as the flow of gas within the gas flow conduit increases such that the flexible membrane contacts an inner surface of a stabilizing conduit. The interaction between the flexible membrane and the stabilizing conduit reduces the vibrations created by the flow of gas past the valve member.

19 Claims, 5 Drawing Sheets

PNEUMATIC VIBRATION DAMPENING DEVICE

BACKGROUND OF THE INVENTION

The present disclosure generally relates to a vibration dampening device. More specifically, the present disclosure relates to a gas flow valve that includes a vibration dampening device to reduce the oscillations and vibrations created by the flow of gas around a movable valve member.

In many mechanical ventilators used with patients to assist breathing, a supply of breathing gas is supplied to the patient from a bellows driven by a pressurized supply of gas. During operation of the ventilator, one or more check valves are positioned between the supply of gas and the bellows. During the inspiratory phase of breathing, the supply of gas is provided to the bellows to cause the bellows to deflate and thus provide breathing gas to the patient. When an inspiratory gas flow valve opens, gas flows past a valve member in the gas flow valve and toward the bellows. Although the flow of gas is relatively constant, variations in the flow rate can create oscillation in the movement of the valve member. The oscillations created by the flow of gas around the valve member can create fluctuations in the fluid stream. These fluctuations are sensed at downstream monitoring locations within the ventilation system and can affect the operation of the ventilation system.

Previously available devices have been used to reduce the amount of vibrations and fluctuations in the gas flow. One of these prior art devices is referred to as a dash pot, which is a bulky item and functions as shock absorbers. Since the dash pots can be both bulky and expensive, it is oftentimes undesirable to include a dash pot in a ventilator.

SUMMARY OF THE INVENTION

The present disclosure generally relates to a gas flow valve that includes a vibration dampening device to reduce the oscillations and vibrations created by the flow of gas around a movable valve member. Specifically, the movable valve member includes a flexible membrane that engages a stabilizing conduit during the movement of the valve member between a seated position and a flow position.

In many applications, a gas flow valve is positioned within a gas flow conduit to control the flow of gas through the gas flow conduit. The gas flow conduit includes a discharge opening that receives the gas flow valve. The gas flow valve includes a valve member that is movable between a seated position to prevent gas flow through the discharge opening and a flow position in which the valve members moves away from the discharge opening to permit the flow of gas through the discharge opening. The valve member can be biased into the seated position in many different manners, such as by gravity or by a spring bias force. When the flow of gas behind the valve member increases, the valve member moves from the seated position to the flow position against the bias force.

The valve member includes a gas passage that extends through the valve member from an inlet opening to an outlet opening. The gas passage is formed such that the inlet opening of the gas passage receives the flow of gas in the gas flow conduit when the valve member is in its seated position. The flow of gas passes through the gas passage and exits through an outlet opening.

A flexible membrane is mounted to an end of the valve member that includes the outlet opening. The flexible membrane includes a fluid tight seal with the valve member such that the gas flow from the gas passage enters into the flexible membrane and is entrapped therein.

When the flow of gas within the gas flow conduit increases, the flexible membrane begins to inflate until an outer surface of the flexible membrane contacts an inner surface of a stabilizing conduit. In one embodiment of the disclosure, the flexible membrane is selected such that the flexible membrane inflates and contacts the stabilizing conduit prior to movement of the valve member from the seated position to the flow position. Since the flexible member inflates into frictional contact with the stabilizing conduit prior to movement of the valve member, the flexible membrane stabilizes the movement of the valve member to reduce vibrations and oscillations created by the flow of gas past the valve member.

When the flow of gas through the gas flow conduit decreases, the valve member moves from the flow position to the seated position to again prevent the flow of gas through the gas flow conduit. The flexible membrane is designed such that the flexible membrane deflates prior to movement of the valve member from the flow position to the seated position. Thus, the flexible membrane stabilizes the movement of the valve member from the seated position to the flow position and allows the valve member to move from the flow position to the seated position as a result of the bias force included in the valve.

In another embodiment of the disclosure, the gas passage formed in the valve member includes two radially spaced outlet openings. The two radially spaced outlet openings are each surrounded by a separate flexible membrane such that the valve member includes a pair of flexible membranes. The pair of flexible membranes inflate and deflate to stabilize the movement of the valve member between the seated position and the flow position.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION OF THE INVENTION

Figure 1:
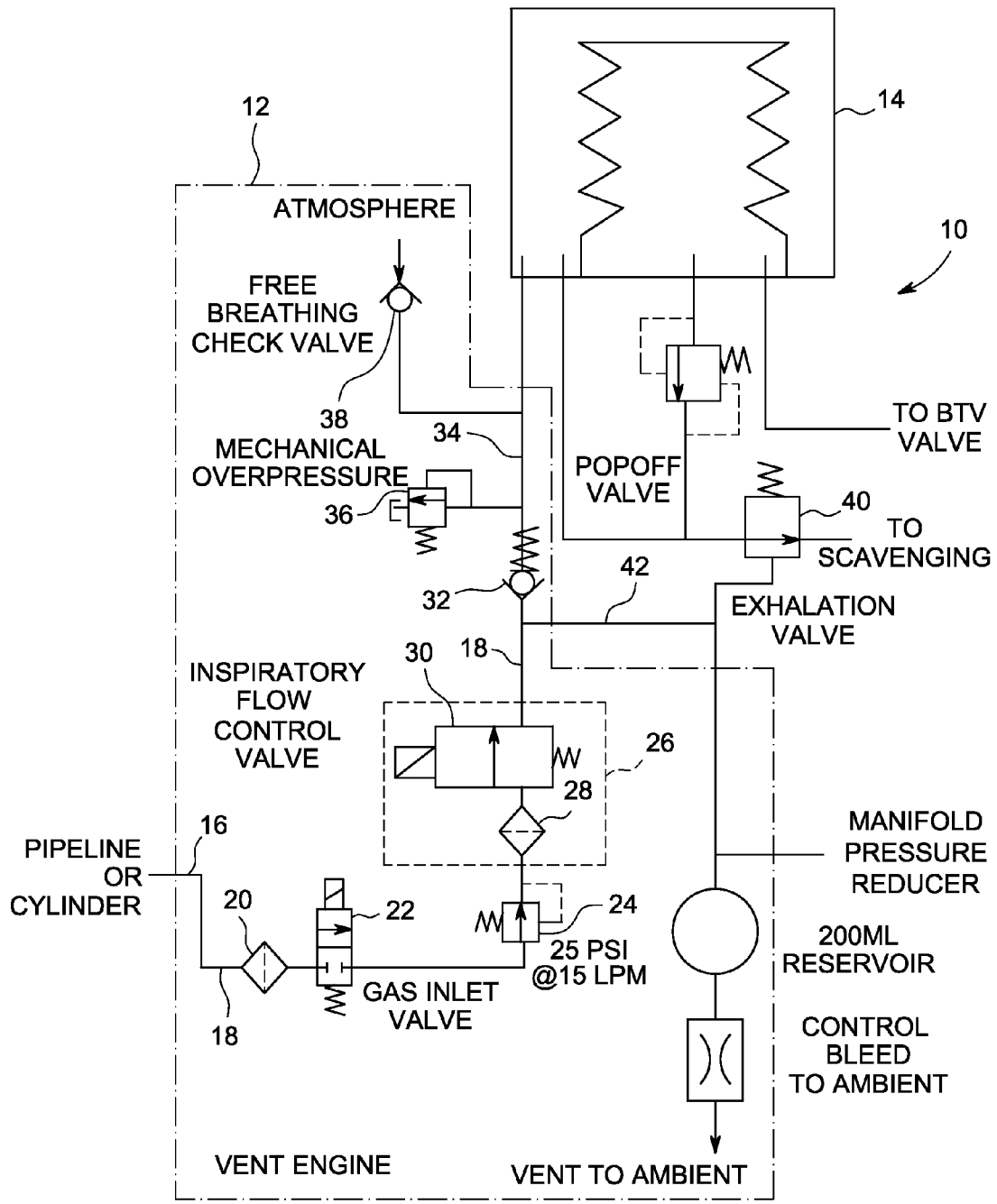
FIG. 1 is a schematic illustration of the flow components included in a typical mechanical ventilation system.

FIG. 1 illustrates a mechanical ventilation system 10 that supplies breathing gas to a patient. The ventilation system 10 generally includes a ventilation engine 12 that drives a bellows 14 to supply a breathing gas to a patient. The ventilation engine 12 receives a supply of pressurized gas at a gas inlet 16 for a gas flow conduit 18. The gas flow within the conduit 18 flows through a filter 20 and a gas inlet valve 22. The gas inlet valve 22 is controlled by a control unit of the ventilation system.

The flow of gas within the conduit 18 flows from the gas inlet valve 22 to a regulator 24 that delivers gas at a regulated pressure and flow rate. In the embodiment shown in FIG. 1, gas from the regulator 24 is delivered at 25 psi at 15 LPM.

An inspiratory flow control valve assembly 26 receives the flow of gas from the regulator 24. The flow control valve assembly 26 includes another filter 28 and a control valve 30. The control valve 30 is selectively opened and closed to provide gas flow to the bellows 14. The control valve 30 is also controlled by a control unit of the ventilator. The timing of the opening and closing of the inspiratory flow control valve assembly 26 controls the breathing rate for the patient receiving ventilation.

The gas flow conduit 18 extends from the inspiratory flow control valve 26 to the bellows 14 through a gas flow valve 32. The gas flow valve 32 functions as a check valve and is biased to the closed position, as illustrated in FIG. 1. In the embodiment of the disclosure shown in FIG. 1, the gas flow valve 32 is biased into the closed position through the force of gravity. However, the bias force in the gas flow valve 32 could be provided by other sources, such as a spring.

When the gas flow within the portion of the gas flow conduit 18 between the flow control valve 26 and the gas flow valve exceeds the bias force of the gas flow valve 32, the gas flows past the gas flow valve 32 and into the portion of the gas flow conduit illustrated by reference numeral 34 and into the bellows 14. An over pressure valve 36 provides an additional safety measure to ensure that the pressure within the flow conduit 34 does not exceed a maximum pressure value.

A free breathing check valve 38 is in fluid communication with atmosphere such that should the patient begin to breath on their own, inlet air can be provided from atmosphere into the bellows chamber.

As illustrated in FIG. 1, the portion of the gas flow conduit 18 extending between the flow control valve 26 and the gas flow valve 32 is in fluid communication with an exhalation valve 40 through a bypass line 42.

During operation of the ventilation system 10 shown in FIG. 1, when the inspiratory flow control valve assembly 26 begins to open, the flow of gas from the flow control valve assembly 26 flows through the bypass line 42 to close the exhalation valve 40. As the pressure continues to build within the gas flow conduit 18 downstream from the flow control valve assembly 26, the gas pressure will eventually exceed the bias force created within the gas flow valve 32. Once the gas pressure exceeds the bias force, the gas flow valve 32 opens and gas flows past the gas flow valve 32 and into the portion of the flow conduit 34.

Once the inspiratory phase has been completed, the inspiratory control valve assembly 26 closes, which reduces the gas pressure within the gas flow conduit 18. Once the inspiratory control valve assembly 26 closes, the gas contained within the bypass line 42 is directed through a reservoir 44 and vented to atmosphere. Since the pressure has been removed from the exhalation valve 40, the exhalation valve 40 again opens and allows the patient to exhale through the exhalation valve 40. As the inspiratory control valve assembly 26 closes, the gas pressure within the gas flow conduit 18 is reduced such that the bias force created within the gas flow valve 32 causes the gas flow valve 32 to close and prevent gas flow past the valve 32. The process identified above is repeated for each inspiratory and expiratory phase of the breathing cycle.

As previously described, during flow of inhalation gases through the gas flow conduit 18, the gas flows through the gas flow valve 32. Although the pressure regulator 24 aids in regulating the flow of gas past the gas flow valve 32, oscillations and vibrations can be introduced into the flow of gas to the bellows 14. In accordance with the present disclosure, the gas flow valve 32 is designed to include a pneumatic vibration dampening device to reduce the amount of vibrations and oscillations created by the flow of gas past the gas flow valve 32.

Figure 2:
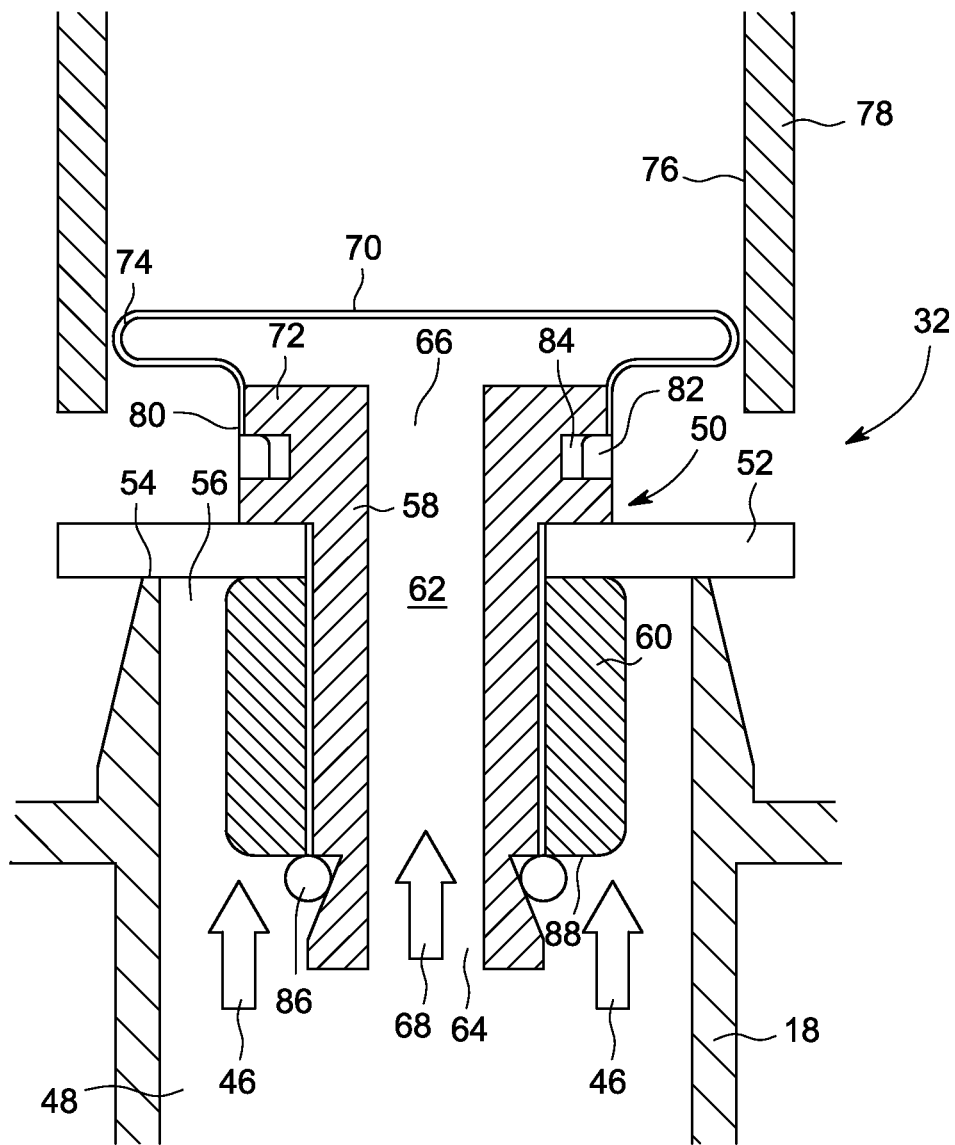
FIG. 2 is a section view of a pneumatic vibration dampening device included in a gas flow valve of the present disclosure.

FIG. 2 illustrates a first embodiment of the gas flow valve 32 constructed in accordance with the present disclosure. The gas flow valve 32 is positioned within the gas flow conduit 18. The gas flow conduit 18 receives a flow of gas, as illustrated by arrows 46 in FIG. 2. When the flow of gas within the open interior 48 of the gas flow conduit 18 is low, a valve member 50 is in the seated position shown in FIG. 2. In the seated position, a sealing ring 52 formed as part of the valve member 50 contacts an outer rim 54 that defines a discharge opening 56 for the gas flow conduit 18.

In the embodiment shown in FIG. 2, the sealing ring 52 surrounds a main body portion 58 of the valve member 50. The main body portion 58 includes a cylindrical weight ring 60 that creates the bias force to hold the sealing ring 52 in the seated position shown in FIG. 2. The weight ring 60 can be formed of a relatively dense material to increase the weight of the valve member 50. In the embodiment shown in FIG. 2, gravity creates the bias force required to hold the sealing ring 52 against the outer rim 54 of the gas flow conduit 18. However, other types of bias force, such as a spring-created bias force, are contemplated as being within the scope of the present disclosure.

The main body 58 of the valve member 50 includes a gas passage 62 that extends from an inlet opening 64 to an outlet opening 66. The inlet opening 64 is positioned below and thus upstream of the discharge opening 56 such that a portion of the gas flow, illustrated by arrow 68, enters the gas passage even when the valve member is in the seated position.

In the embodiment shown in FIG. 2, a flexible membrane 70 is attached to an upper end 72 of the body portion 58 of the valve member 50. The flexible membrane 70 is circular and extends radially outward to a radial edge 74. In the relaxed condition shown in FIG. 2, the radial edge 74 contacts an inner surface 76 of a stabilizing conduit 78. However, in the flaccid condition shown in FIG. 2, the radial edge 74 does not exert a radial force on the inner surface 76 since the membrane 70 is not inflated and is flexible. In an alternate configuration, the size of the flexible membrane could be such that the flexible membrane would not contact the inner surface 76 until the flexible membrane is inflated.

In the embodiment shown in FIG. 2, the flexible membrane 70 has an outer edge 80 that is attached to the body portion 58 by a flexible O-ring 82. The O-ring 82 is seated within a recessed groove 84 formed in the body portion 58. The O-ring 82 creates a fluid tight seal between the flexible membrane 70 and the body portion 58 to secure the flexible membrane 70 to the body portion 58 such that the flexible membrane 70 surrounds the outlet opening 66 formed as part of the gas passage 62.

An O-ring 86 is positioned between the main body 58 and the lower end 88 of the weight ring 60. The O-ring 86 prevents gas flow between the gap created by the physical interaction between the weight ring 60 and the outer surface of the body portion 58.

Figure 3:
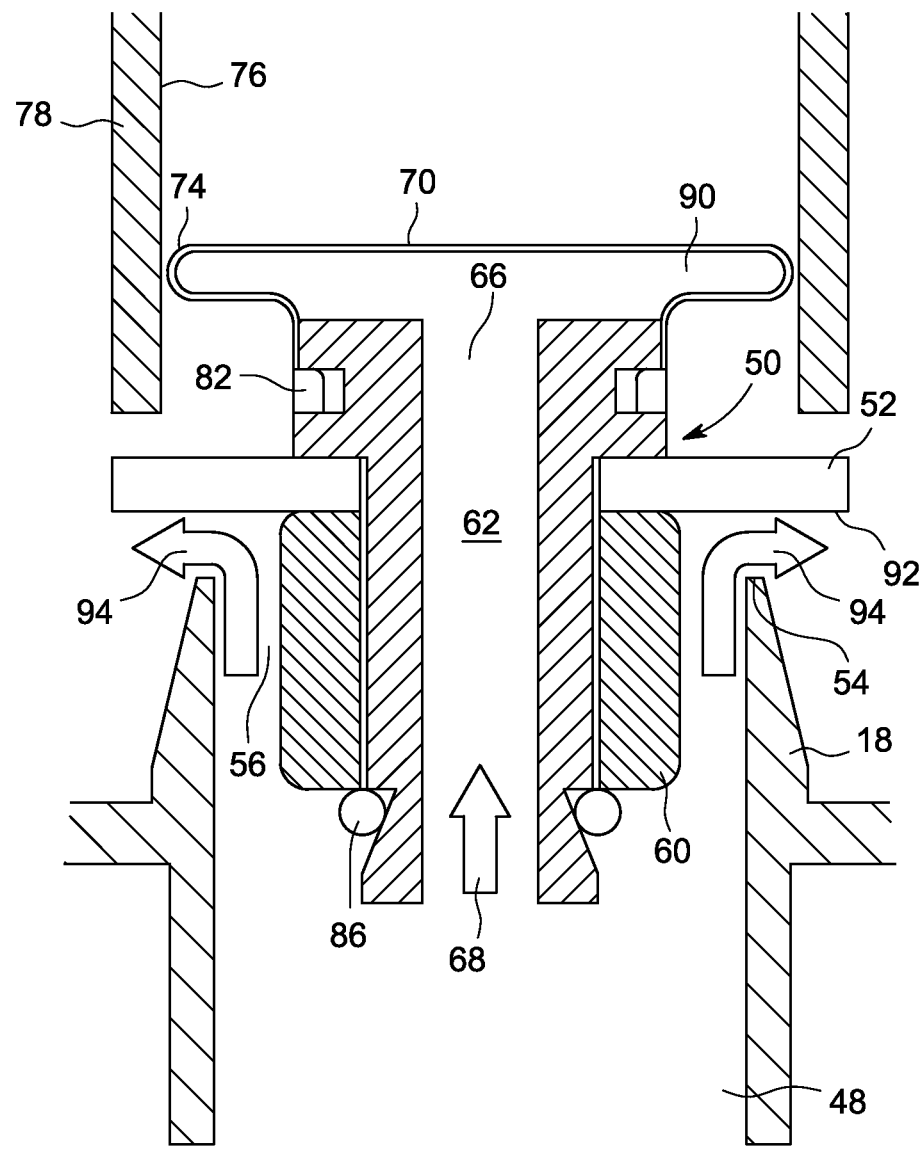
FIG. 3 is a section view similar to FIG. 2 illustrating the movement of a valve member from the seated position of FIG. 2 to the flow position.

When the gas flow increases within the gas flow conduit 18, such as when the inspiratory flow control valve assembly 26 shown in FIG. 1 opens, the increased flow of gas creates a pressure differential across the membrane 70. The pressure differential causes the flexible membrane 70 to expand, as shown in FIG. 3. When the flexible membrane 70 expands, the size of the open interior 90 increases and the radial edge 74 presses against the inner surface 76 of the stabilizing conduit 78. The inflation of the flexible membrane 70 creates a frictional interaction between the radial edge 74 and the inner surface 76. The frictional interaction restricts the vertical movement of the valve member 50. The restricted movement acts as a damper to reduce the vibrations and oscillations created by the flow of gas between the lower surface 92 of the sealing ring 52 and the outer rim 54 that defines the discharge opening 56. This flow of gas is illustrated by arrows 94 in FIG. 3.

In the embodiment shown in FIG. 3, the valve member 50 has moved from the seated position of FIG. 2 to a flow position in which the sealing ring 52 is spaced from the outer rim 54 to allow the flow of gas illustrated by arrow 94. As previously described, when the flow of gas is sufficient to overcome the bias force created by the weight ring 60, the valve member 50 moves to the flow position shown in FIG. 3.

In the position shown in FIG. 3, the flexible membrane 70 is inflated and the valve member 50 is moved to its flow position. The flexible membrane 70 is designed such that the flexible membrane 70 inflates based upon the gas flow illustrated by arrow 68 prior to movement of the valve member 50 from the seating position of FIG. 2 to the flow position of FIG. 3. In this manner, the flexible membrane 70 contacts the inner surface 76 of the stabilizing conduit to prevent oscillation of the valve member, as described.

When the inspiratory flow control valve assembly closes and reduces the gas flow within the open interior 48, the bias force on the valve member 50 causes the valve member 50 to return to the seated position shown in FIG. 2. When the gas flow rate decreases further, the flexible membrane 70 begins to deflate until the flexible membrane returns to the deflated condition shown in FIG. 2. The flexible membrane is selected such that the flexible membrane inflates prior to and during movement of the valve member from the seated position to the flow position and deflates to allow the valve member 50 to return to the seated position from the flow position. The inflation of the flexible membrane 70 is controlled by the material selected for the flexible membrane as well as the thickness of the material that forms the flexible membrane.

Figure 4:
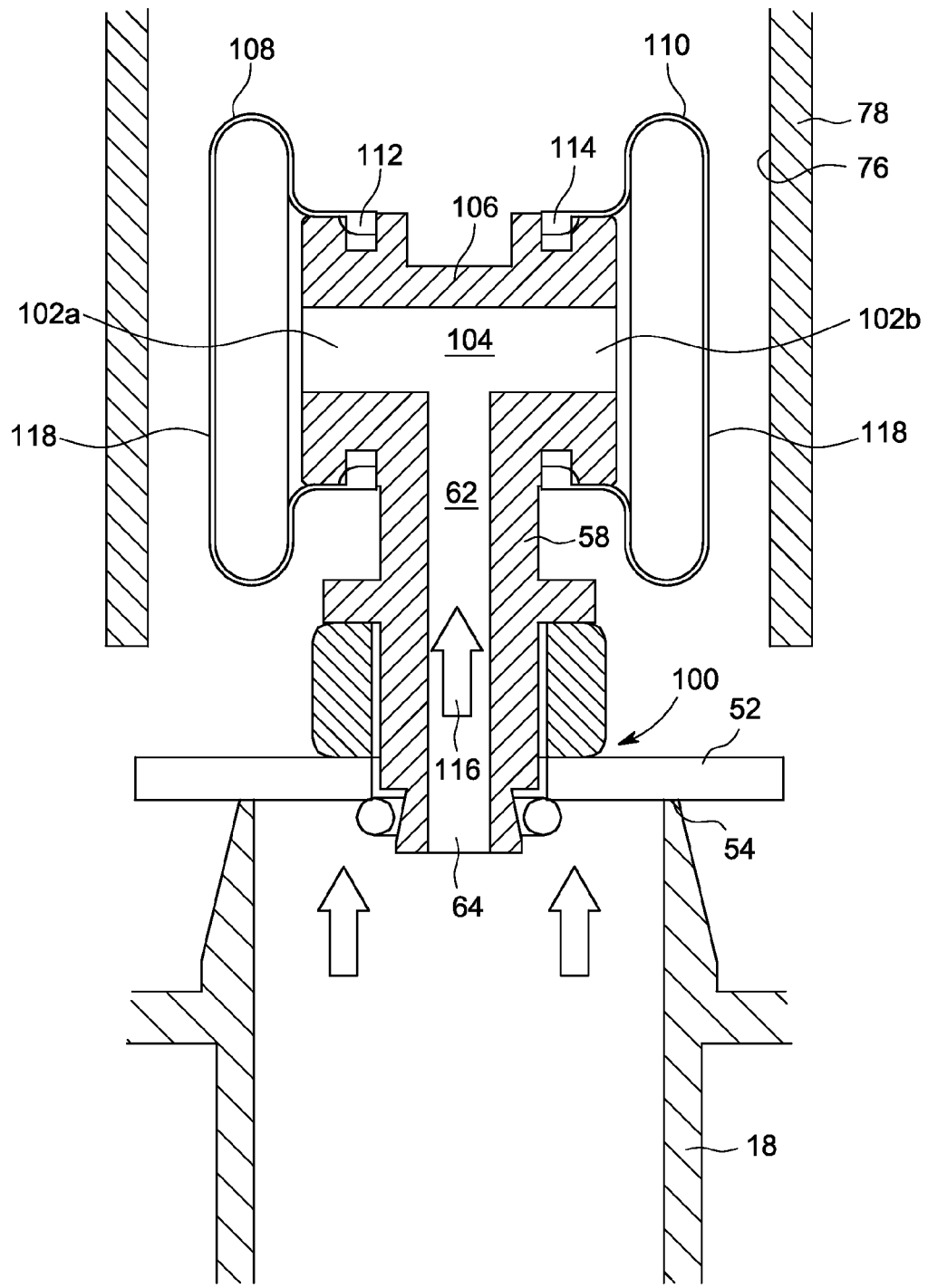
FIG. 4 is a section view of a second embodiment of a pneumatic vibration dampening device included in the gas flow valve when the valve member is in the seated position.
Figure 5:
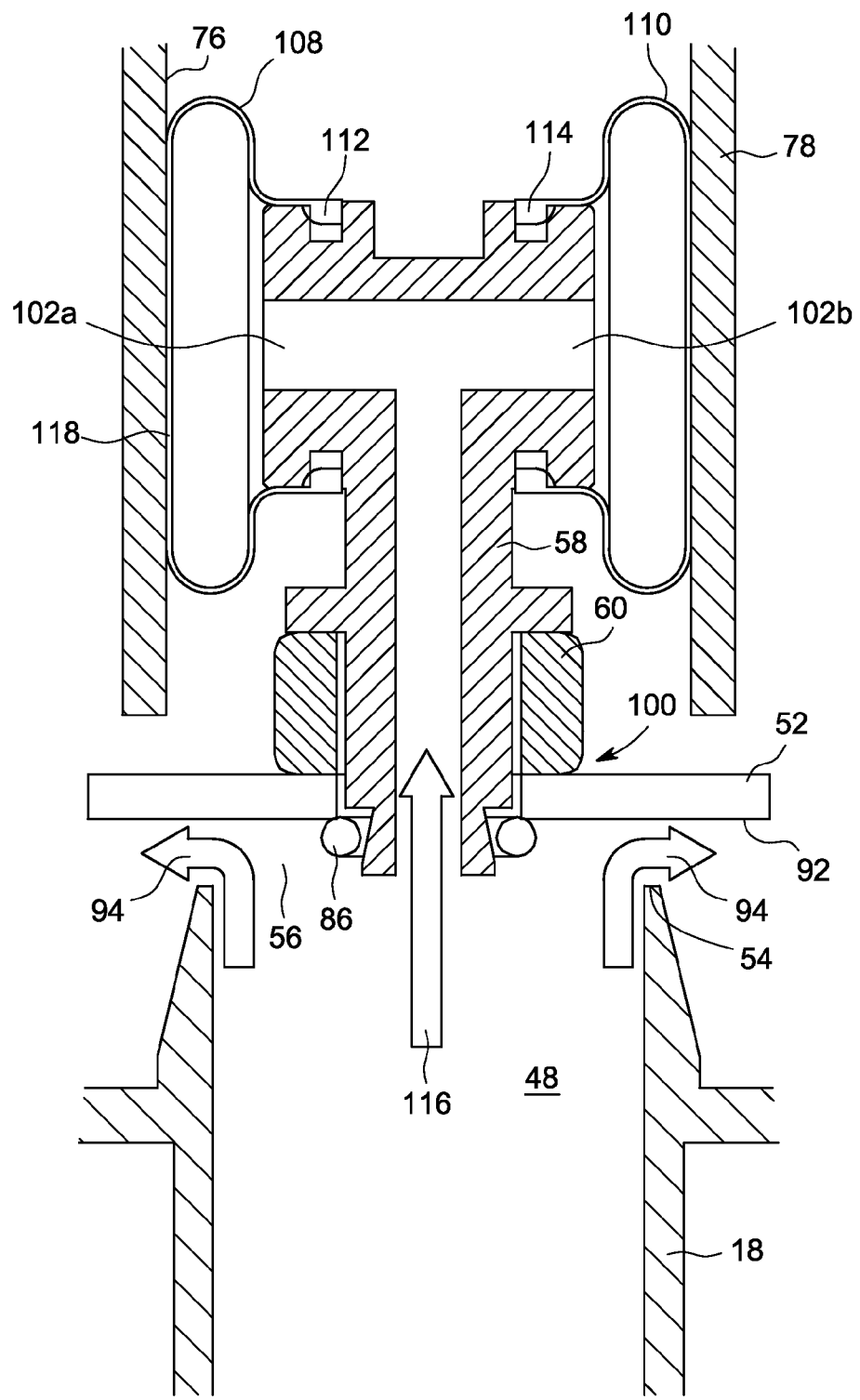
FIG. 5 is a section view of the embodiment shown FIG. 4 illustrating the movement of the valve member from the seated position of FIG. 4 to a flow position.

Referring now to FIGS. 4 and 5, thereshown is a second embodiment of the valve member 100. The valve member 100 functions in nearly the same way as the valve member 50 shown in FIGS. 2 and 3. Similar reference numerals will be utilized for similar components in the embodiment shown in FIGS. 4 and 5.

The valve member 100 includes the gas passage 62 extending from the inlet opening 64 to a pair of outlet openings 102a and 102b. The pair of outlet openings 102 are formed as part of a transverse gas passage 104. The transverse gas passage 104 connects to the gas passage 62 and extends outward in a radial direction. In the embodiment shown in FIG. 4, the upper end 106 of the body portion 58 receives a first flexible membrane 108 and a second flexible membrane 110. The first flexible membrane is held onto the upper end 106 by a first O-ring 112 while the second flexible membrane 110 is held in place by a second O-ring 114. As illustrated in FIG. 4, the first flexible membrane 108 surrounds the first outlet opening 102a while the second flexible membrane 110 surrounds the second outlet opening 102b.

When the flow of gas is low and insufficient to cause the valve member 100 to move from the seated position shown in FIG. 4, the sealing ring 52 engages the outer rim 54 to prevent the flow of gas around the valve member 100. As the flow of gas increases, the gas flow travels into the gas passage 62, as illustrated by arrow 116. The flow of gas 116 travels upward within the gas passage 62 and enters the transverse gas passage 104. The gas flow travels out of the pair of opposite outlet openings 102a and 102b and begins to inflate the first flexible membrane 108 and the second flexible membrane 110. As the flexible membranes 108 and 110 begin to inflate, an outer surface 118 of each membrane begins to move outward toward an inner surface 76 of the stabilizing conduit 78. When the gas flow reaches a sufficient value, the outer surface 118 engages the inner surface 76 of the stabilizing conduit 78.

As the gas flow continues to increase, the valve member 100 moves upward until the sealing ring 52 creates a gap between the lower surface 92 and the outer rim 54 that defines the discharge opening 56, as shown in FIG. 5. Gas flows through this opening as illustrated by arrows 94. The interaction between the first and second flexible membranes 108 and 110 reduce the vibrations and oscillations caused by the flow 94.

Once the inspiratory phase has been completed, the inspiratory flow control valve assembly closes, which reduces the flow within the open interior 48 of the gas flow conduit 18. As the flow rate is reduced, the bias force created by the weight ring 60 moves the valve member 100 from the flow position shown in FIG. 5 to the seated position shown in FIG. 4. As with the first embodiment, the first and second flexible membranes 108, 110 are configured such that the first and second flexible membranes 108, 110 are deflated to allow the valve member 100 to move to the seated position shown in FIG. 4. Thus, the frictional interaction between the outer surface 118 of each flexible membrane 108, 110 and the stabilizing conduit 78 is removed to allow the valve member 100 to return to the seated position shown in FIG. 4. Once again, the thickness and type of material used to create the flexible membranes 108, 110 is selected to insure that the flexible membranes inflate and deflate at the proper time relative to the movement of the valve member 100 between the seated and flow positions.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims

I claim:

1. A gas flow valve comprising:
   a gas flow conduit having a discharge opening, wherein the gas flow conduit receives a flow of gas to be regulated by the gas flow valve;
   a valve member movable between a seated position to prevent gas flow through the discharge opening and a flow position in which the valve member moves away from the discharge opening to permit the flow of gas through the discharge opening;
   a gas passage formed in the valve member; and
   at least one flexible membrane mounted to the valve member and in fluid communication with the gas passage, wherein the gas flow inflates the flexible membrane to stabilize the movement of the valve member as the valve member transitions from the seated position to the flow position.

2. The gas flow valve of claim 1 wherein the gas passage extends from an inlet opening to an outlet opening, wherein the inlet opening is located within the gas flow conduit to receive the gas flow when the valve member is in the seated position.

3. The gas flow valve of claim 2 wherein the flexible membrane surrounds the outlet opening such that the flow of gas within the gas flow conduit is received within the flexible membrane through the gas passage.

4. The gas flow valve of claim 1 wherein the valve member is biased into the seated position and wherein the gas flow inflates the flexible membrane before the gas flow moves the valve member from the seated position to the flow position.

5. The gas flow valve of claim 4 further comprising a stabilizing conduit surrounding the flexible membrane, wherein the flexible membrane inflates into contact with the stabilizing conduit to stabilize movement of the valve member.

6. The gas flow valve of claim 4 wherein the valve member is biased into the seated position by gravity.

7. A device for dampening vibration caused by the flow of gas through a discharge opening of a gas flow conduit, the device comprising:
   a valve member movable between a seated position to prevent gas flow through the discharge opening and a flow position in which the valve member moves away from the discharge opening to permit fluid flow through the discharge opening;
   a gas passage formed in the valve member extending from an inlet opening to an outlet opening;
   at least one flexible membrane mounted to the valve member and surrounding the outlet opening of the gas passage such that the flexible membrane is in fluid communication with the gas passage, wherein the gas flow within the gas flow conduit inflates the flexible membrane; and
   a stabilizing conduit surrounding the flexible membrane, wherein the flexible membrane inflates into contact with the stabilizing conduit to stabilize movement of the valve member.

8. The device of claim 7 wherein the gas passage receives the gas flow from the gas flow conduit when the valve member is in the seated position.

9. The device of claim 7 wherein the gas passage includes two outlet openings and the gas flow valve includes two flexible membranes, wherein each of the flexible membranes surrounds one of the outlet openings.

10. The gas flow valve of claim 9 wherein the valve member is biased into the seated position by gravity.

11. The gas flow valve of claim 10 further comprising a stabilizing conduit surrounding the flexible membranes, wherein the flexible membrane inflates into contact with the stabilizing conduit.

12. The device of claim 7 wherein the valve member is biased into the seated position and wherein the gas flow inflates the flexible membrane before the gas flow moves the valve member from the seated position to the flow position.

13. The device of claim 12 wherein the valve member is biased into the seated position by gravity.

14. A gas flow valve for use in a gas supply conduit of a ventilator, comprising:
   a valve member movable within a stabilizing conduit between a seated position to prevent gas flow through the gas conduit and a flow position to permit the flow of gas through the gas conduit;
   a gas passage formed in the valve member, the gas passage having an inlet opening and an outlet opening, wherein the inlet opening receives the gas flow when the valve member is in the seated position; and
   at least one flexible membrane mounted to the valve member and surrounding the outlet opening of the gas passage, wherein gas flows into the flexible membrane to inflate the flexible membrane to cause the flexible membrane to contact the stabilizing conduit.

15. The gas flow valve of claim 14 wherein the valve member is biased into the seated position and wherein the gas flow inflates the flexible member before the gas flow moves the valve member from the seated position to the flow position.

16. The gas flow valve of claim 15 wherein the gas passage includes two outlet openings and the gas flow valve includes two flexible membranes, wherein each of the flexible membranes surrounds one of the outlet openings.

17. A gas flow valve comprising:
   a gas flow conduit having a discharge opening, wherein the gas flow conduit receives a flow of gas to be regulated by the gas flow valve;
   a valve member movable between a seated position to prevent gas flow through the discharge opening and a flow position in which the valve member moves away from the discharge opening to permit the flow of gas through the discharge opening;
   a gas passage formed in the valve member having an inlet opening and at least two outlet openings, wherein the inlet opening is located within the gas flow conduit to receive the gas flow when the valve member is in the seated position; and
   two flexible membranes, one surrounding each of the at least two outlet openings such that the flow of gas within the gas flow conduit is received within the flexible membranes through the gas passage, wherein the gas flow inflates the flexible membranes to stabilize the movement of the valve member.

18. The gas flow valve of claim 17 wherein the valve member is biased into the seated position and wherein the gas flow inflates the flexible membranes before the gas flow moves the valve member from the seated position to the flow position.

19. The gas flow valve of claim 18 further comprising a stabilizing conduit surrounding the valve member, wherein the flexible membranes inflate into contact with the stabilizing conduit.

* * * * *